United States Patent [19]

van den Berg et al.

[11] Patent Number: 5,349,075
[45] Date of Patent: Sep. 20, 1994

[54] CONTINOUS ESTERIFICATION OF CARBOXYLIC AND FATTY ACIDS IN THE ABSENSE OF A CATALYST

[75] Inventors: Hendrikus J. van den Berg, Doetinchen; Robbert Klob, Vlaardinger, both of Netherlands

[73] Assignee: Unilever Patent Holdings B.V., Rotterdam, Netherlands

[21] Appl. No.: 630,990

[22] Filed: Dec. 21, 1990

[30] Foreign Application Priority Data

Dec. 22, 1989 [EP] European Pat. Off. ........ 89203343.2
Nov. 19, 1990 [GB] United Kingdom ................ 9025081

[51] Int. Cl.$^5$ ............................................. C11C 3/00
[52] U.S. Cl. .................................. 554/170; 550/172; 550/173; 560/205; 560/224; 560/231; 560/263; 560/265
[58] Field of Search ................ 554/170, 172, 173; 560/205, 224, 231, 263, 268

[56] References Cited

U.S. PATENT DOCUMENTS

| | | | |
|---|---|---|---|
| 4,314,947 | 2/1982 | Hohenschutz | 554/173 |
| 4,868,329 | 9/1989 | Powando et al. | 554/172 |
| 5,008,046 | 4/1991 | Bremus et al. | 554/172 |

FOREIGN PATENT DOCUMENTS

| | | | |
|---|---|---|---|
| 1908517 | 9/1969 | Fed. Rep. of Germany . | |
| 02775 | 4/1988 | PCT Int'l Appl. | C12N 9/20 |
| WO90/08127 | 7/1990 | PCT Int'l Appl. | C07C 67/08 |
| 465983 | 5/1937 | United Kingdom . | |
| 1430069 | 3/1976 | United Kingdom | C07C 69/34 |

OTHER PUBLICATIONS

Chemical Abstracts, 72(6)22792y.

Primary Examiner—José G. Dees
Assistant Examiner—Deborah D. Carr
Attorney, Agent, or Firm—Cushman, Darby & Cushman

[57] ABSTRACT

The invention provides a process for the esterification of a $C_2$-$C_{24}$ monocarboxylic acid with a $C_1$-$C_5$ monoalcohol in a reactor at an increased reaction temperature and increased pressure which is carried out in the absence of any esterification catalyst while continuously feeding in the alcohol during the reaction and removing a gaseous alcohol/water mixture. Preferably the process is carried out in countercurrent in column reactor which is packed or contains plates. The reaction temperature is usually between 200° C. and 260° C. at a pressure between 0.5 and 1.5 MPa. There is a $C_6$-$C_{20}$ monocarboxylic acid and monoalcohol a $C_1$-$C_3$ monoalcohol. More preferably the process is carried in two steps with a first step as described above and a second step in which further reaction to a conversion of at least 99% is carried out in the presence of an esterification catalyst at a temperature below 100° C.

8 Claims, No Drawings

CONTINOUS ESTERIFICATION OF CARBOXYLIC AND FATTY ACIDS IN THE ABSENSE OF A CATALYST

The invention relates to a process for the esterification of an acid with an alcohol. More in particular the invention relates to such a process in which the esterification is carried out in a reactor at an elevated reaction temperature and an elevated pressure.

It is known in the art to carry out esterification reactions in the presence of an esterification catalyst whilst dosing carboxylic acid and alcohol in countercurrent in a column reactor. The catalyst is usually an acidic catalyst such as a sulfonic acid, a base such as an alkalihydroxide or an alkali alcoholate, a metal oxide or a metal alkylate. Such processes are disclosed inter alia in DE-A-2 503 195 (Henkel) and EP-A-334 154 (Henkel).

It has been found that the esters prepared by these processes, especially when prepared at elevated reaction temperature and/or at elevated pressure, as a rule contain appreciable amounts of contaminants caused by presence of the catalyst. For instance sulphur compounds from customary sulphonic acid type catalysts may be present. Also, especially when acid catalysts are used, as a side-reaction dehydration of the alcohol occurs, leading to the production of alkenes and/or ethers, which reaction is favoured by the increased reaction temperature and increased pressure. Elaborate purification processes have been necessary, especially when the catalyst was soluble in the reaction mixture.

In a few cases the prior art discloses a process for the esterification of a monocarboxylic acid with a lower alcohol at elevated temperature and under pressure in the absence of any esterification catalyst, but these processes normally result only in partial conversion of the carboxylic acid into ester. With a considerable excess of alcohol a conversion of 95% appears to be typical. Such processes are disclosed for instance in NL-B- 92 089 (Societe Belge de l'azote..) and in Chemical Abstracts 72, 022792y (1968).

In order to obtain purer esters is has also been proposed to carry out the esterification reaction in the presence of a enzyme such as lipase. Although such processes yield very good quality esters they are not easy to operate. Processes of this type are disclosed inter alia in WO-A-88/02775 (Novo Industries).

The present invention provides a process for the esterification of a carboxylic acid with an alcohol at an elevated temperature and pressure, characterised in that the reaction takes place in a reactor in the absence of a catalyst by continuously feeding one reactant in the gaseous phase and the other reactant in the liquid phase to the reactor and continuously removing therefrom a gaseous mixture the more volatile reactant and water.

Thus it follows that the process is applicable where one reactant is more volatile than the other and that at the temperature and pressure at which the process is carried out, the more volatile reactant is in the gaseous phase while the less volatile reactant is in the liquid phase.

By the term "catalyst" is to be understood inorganic materials, organo metal compounds, and organic compounds such as enzymes (biocatalysts). In such a process the excess volatile reactant is used as an entraining agent to remove the water of reaction and this technique therefore can yield very high conversion percentages. Moreover the amount of contaminants formed is small because the reaction is carried out in the absence of any catalyst.

Either the carboxylic acid or the alcohol constitutes the more volatile reactant. The carboxylic acid may be a monocarboxylic acid.

In one embodiment the carboxylic acid is a monocarboxylic acid present as a liquid in an autoclave and alcohol vapour is passed through or over the liquid, the excess alcohol vapour entrails the water of reaction formed so that the reaction is driven to completion. Very high conversion percentages can be obtained this way.

In a preferred embodiment of the invention the esterification is carried out in countercurrent in column reactor which is packed or contains plates. The plates may have holes or bubble caps to facilitate contact between the reactants and improves mass transport.

In a preferred embodiment the reaction temperature during the esterification is between 200° C. and 260° C. and the pressure between 0.5 and 1.5 MPa.

The carboxylic acid is a monocarboxylic acid. Suitable monocarboxylic acid starting materials contain 2 to 24, preferably 6 to 20 carbon atoms in the molecule. The carboxylic acid may contain one or more double bonds in the molecule and usually it is a straight chain carboxylic acid. Suitable non-volatile carboxylic acids are caprylic acid, capric acid, lauric acid, myristic acid, palmitic acid, stearic acid, oleic acid, linoleic acid as well as dimeric and trimeric fatty acids. Mixtures of the above acids as can be used. When the carboxylic acid is the volatile reactant, suitable examples include acetic acid and propanoic acid. Carboxylic acids of intermediate volatility, such as valeric acid, may act as the volatile or the non-volatile component according to the temperature and pressure at which the esterification reaction is carried out.

The alcohol starting material is preferably a monohydric or dihydric alcohol. Suitable volatile alcohols contain 1 to 5, preferably 1 to 3 carbon atoms in the molecule. Preferably the alcohol is a primary alcohol. Suitable volatile alcohols are methanol, ethanol, propanol, isopropanol, a butanol, a pentanol or 2-ethyl hexanol.

When the alcohol is the non-volatile component, suitable monoalcohol examples have from 12 to 24 carbon atoms such as lauryl alcohol, myristyl alcohol, and cetyl alcohol, while suitable polyol examples include ethylene glycol, trimethylene glycol, tetramethylene glycol, neopentylglycol, pentamethylene glycol and glycerol.

It is generally preferred to add the volatile reactant to the non-volatile reactant in the form of a heated vapour.

In a further preferred embodiment of the invention the process is carried in two steps with a first step in the absence of any esterification catalyst and a reaction temperature of at least 200° C. resulting in a conversion of the non-volatile reactant into ester of at least 85%, such as at least 93%, preferably at least 96%, followed by a second step in which further reaction to a conversion of at least 99% is carried out with an excess of the volatile reactant in the liquid phase in the presence of an esterification catalyst at a temperature below 100° C. In view of the presence of the catalyst and the required further esterification of at most some 7% of residual non-volatile reactant in the second step only a relatively short residence time at a relatively low reaction temperature is needed, so that contamination of the ester with the products of side-reactions and fragments of the catalyst is minute. Very high conversion percentages of more than 99% can thus be achieved.

The catalyst employed in this second step is preferably an acidic esterification catalyst. Also preferably the catalyst is insoluble in the reaction medium. Clearly suitable catalysts are certain acids, bases and oxides. Insoluble materials e.g. resins containing sulfonic acid groups are very suitable. Examples are certain cation exchange resins such as sulfonated styrene, p.toluenesulfonic acid attached to Teflon etc. In a further preferred embodiment of this invention the esterification of step 2 is carried out with excess dry or water-free volatile reactant, which is recovered in aqueous form from step 2 and recirculated to step 1.

The invention will now be illustrated by the following non-limiting examples.

EXAMPLE 1

In a 1 liter stirred autoclave filled with 400 g oleic acid (a.v. 199) gaseous methanol was led through at a rate of 90 g methanol per hour (2 moles methanol per mole oleic acid per hour) at a temperature of 240° C. and a pressure of 1 MPa. The water of reaction was removed with the stream of alcohol leaving the reactor. After 3 hours the acid value of the reaction mixture was 6, which is equivalent to a conversion of 97%.

EXAMPLE 2

A technical grade mixture of fatty acids, consisting of 70% oleic acid with about 10% stearic acid and linoleic acid each and 6% of palmitoleic acid and an acid value of 200, was fed continuously at the top tray of a total of nine trays of a stainless steel bubble cap column. Methanol vapour was fed also continuously into the bottom section of the column just below the bottom tray. The temperature of the liquid on the trays in the column was kept at 240° C. and the pressure was kept at 1 MPa. From the top of the column a vapour mixture of methanol and water emitted, which was condensed and collected as a liquid. The product from the bottom of the column was cooled to 50°-70° C. and collected. At a molar ratio of fatty acid to methanol of 1:6 and a residence time of the liquid of 3 hours a methyl ester with an acid value of 4.2 was obtained. Under the same conditions and a residence time of 5 hours a product with an acid value of 1.8 was obtained.

EXAMPLE 3

By using the procedure of Example 2 an ester was produced having an acid value of 6.5. This ester was mixed with excess of dry liquid methanol (water content 0.02% w.w.) and fed to a packed bed of 450 ml strongly acidic ion exchange resin at a temperature of 50° C. The residence time of the ester/methanol mixture calculated on the void fraction of the bed was 20 minutes. At methanol/ester ratios of 2:1, 3:1, and 4:1 respectively esters with acid values of 0.58, 0.43 and 0.74 were obtained.

EXAMPLE 4

Heated vapours of ethanol were led through maleic acid at a temperature of 180°-220° C. at a rate of 6:1 moles per hour for 90 min at atmospheric pressure. The water formed by the reaction evaporated along with the excess ethanol. After evaporating some volatile material from the residue an AV was found of 211. Compared with AV-931 for maleic acid, the conversion was 77%.

EXAMPLE 5

Heated vapours of pentanoic acid (185° C.) were led through TMP (trimethylol propane) at a temperature of 180°-200° C. at a rate of 3.7:1 moles per hour for 1 hour at atmospheric pressure. Water formed during the reaction distilled off along with the excess pentanoic acid. After evaporating as much volatile material as possible, the residue showed $AV=119$ and an OH-value of 11.

EXAMPLE 6

Heated vapours of 2-ethyl-hexanol (bp 185° C.) were led through dimeric fatty acid at a temperature of 205°-230° C. at a rate of 3:1 moles per hour for about 90 min at atmospheric pressure. About 10 ml of water were collected from the vapours by condensation. The residue showed an $AV=8.9$, which, reckoning with an AV of about 100 for the starting material, is equivalent with a conversion of about 90%.

What is claimed is:

1. In a process for the esterification of a carboxylic acid with an alcohol in which the reaction temperature is between 200° and 260° C. and the pressure is between 0.5 and 1.5 Mpa, the improvement wherein the reaction takes place in a reactor in the absence of a catalyst by continuously feeding one reactant in the gaseous phase and the other reactant in the liquid phase to the reactor and continuously removing therefrom a gaseous mixture comprising the more volatile reactant and water.

2. A process according to claim 1, wherein the carboxylic acid has from 2 to 24 carbon atoms.

3. A process according to claim 1, wherein the alcohol is a mono functional alcohol.

4. A process according to claim 1, wherein the volatile component is an alcohol with from 1 to 5 carbon atoms.

5. A process according to claim 1 in which the process is carried out in countercurrent in column reactor which is packed or contains plates.

6. A process according to claim 1 in which the non-volatile reactant is a mono- carboxylic acid having from 6 to 20 carbon atoms.

7. A process according to claim 1 in which the volatile reactant is an alcohol having from 1 to 3 carbon atoms.

8. Process according to claim 1 in which the process is carried in two steps with a first step in the absence of any esterification catalyst and a reaction temperature of at least 200° C. resulting in a conversion of the non-volatile reactant into ester of at least 85%, followed by a second step in which further reaction to a conversion of at least 99% is carried out in the liquid phase with an excess of the volatile reactant in the presence of an esterification catalyst at a temperature below 100° C.

* * * * *